(12) United States Patent
Burgett et al.

(10) Patent No.: US 9,706,282 B2
(45) Date of Patent: Jul. 11, 2017

(54) EARPIECE SYSTEM

(75) Inventors: Seth D. Burgett, Glen Carbon, IL (US);
Richard J. Daniels, St. Louis, MO
(US); Michael D. Wetle, St. Louis, MO
(US); David Fishbaine, Minnetonka,
MN (US)

(73) Assignee: Harman International Industries, Incorporated, Stamford, CT (US)

( * ) Notice: Subject to any disclaimer, the term of this patent is extended or adjusted under 35 U.S.C. 154(b) by 1062 days.

(21) Appl. No.: 12/710,903

(22) Filed: Feb. 23, 2010

(65) Prior Publication Data

US 2010/0296664 A1 Nov. 25, 2010

Related U.S. Application Data

(60) Provisional application No. 61/154,502, filed on Feb. 23, 2009.

(51) Int. Cl.
| | |
|---|---|
| H04R 25/00 | (2006.01) |
| A61B 7/02 | (2006.01) |
| H04R 1/10 | (2006.01) |
| A61F 11/08 | (2006.01) |
| G06Q 50/22 | (2012.01) |

(52) U.S. Cl.
CPC ............ *H04R 1/1016* (2013.01); *A61F 11/08* (2013.01); *G06Q 50/22* (2013.01); *H04R 1/1058* (2013.01); *H04R 1/1083* (2013.01)

(58) Field of Classification Search
CPC .............................. A61F 11/08; H04R 1/1016
USPC ........................................... 705/28; 703/6, 1
See application file for complete search history.

(56) References Cited

U.S. PATENT DOCUMENTS

| | | | | |
|---|---|---|---|---|
| 5,592,248 | A | 1/1997 | Norton et al. | |
| 5,729,658 | A * | 3/1998 | Hou ..................... | G10L 25/69 381/60 |
| 5,870,481 | A * | 2/1999 | Dymond ............... | H04R 25/70 381/17 |
| 6,533,062 | B1 * | 3/2003 | Widmer ............... | H04R 25/658 181/129 |
| 6,574,342 | B1 * | 6/2003 | Davis .................... | H04R 25/70 381/314 |
| 6,692,127 | B2 | 2/2004 | Abitbol et al. | |
| 7,394,910 | B2 * | 7/2008 | Smith ................... | H04R 1/1016 381/322 |
| 7,555,356 | B2 * | 6/2009 | Martin Roth ........ | A61B 5/1077 181/129 |
| 7,599,499 | B2 * | 10/2009 | Naylor .................. | H04R 25/70 381/312 |
| 7,922,671 | B2 * | 4/2011 | Zoth ..................... | A61B 5/121 600/372 |
| 8,032,337 | B2 * | 10/2011 | Deichmann .......... | A61F 11/08 345/419 |
| 8,086,427 | B2 * | 12/2011 | Fang .................... | H04R 25/652 345/419 |
| 8,160,284 | B2 * | 4/2012 | Johnson ............... | H03F 1/307 381/312 |

(Continued)

*Primary Examiner* — Talia Crawley
(74) *Attorney, Agent, or Firm* — Brooks Kushman P.C.

(57) ABSTRACT

A system and method for providing earpieces for a user includes an inventory of standard earpieces having a plurality of different parameters, and a device for making a non-contact measurement of the user's ear, such as a camera or scanner. An ear-piece is selected from the inventory based on the non-contact measurement of the user's ear.

8 Claims, 7 Drawing Sheets

(56) References Cited

U.S. PATENT DOCUMENTS

| | | | |
|---|---|---|---|
| 8,295,523 B2* | 10/2012 | Fay | H04R 25/604 381/324 |
| 8,743,377 B2* | 6/2014 | Hart | G01B 11/0658 356/624 |
| 2003/0171996 A1* | 9/2003 | Chen | G06Q 10/08 705/26.81 |
| 2004/0004633 A1 | 1/2004 | Perry et al. | |
| 2004/0107080 A1* | 6/2004 | Deichmann | A61F 11/08 703/6 |
| 2005/0082370 A1 | 4/2005 | Frantz et al. | |
| 2005/0088435 A1* | 4/2005 | Geng | G06T 7/0022 345/419 |
| 2005/0089213 A1* | 4/2005 | Geng | G06K 9/00214 382/154 |
| 2006/0188105 A1* | 8/2006 | Baskerville | A61F 11/08 381/60 |
| 2006/0204013 A1 | 9/2006 | Hannibal et al. | |
| 2008/0152182 A1* | 6/2008 | Bevirt | H04R 1/1058 381/371 |
| 2008/0159560 A1* | 7/2008 | Song | G10L 25/78 381/94.1 |
| 2008/0178088 A1* | 7/2008 | Goldstein | G06Q 30/02 715/727 |
| 2010/0039534 A1* | 2/2010 | Hart | A61B 1/043 348/234 |
| 2010/0076793 A1* | 3/2010 | Goldstein | G06F 21/10 705/4 |
| 2011/0290005 A1* | 12/2011 | Hart | G01B 11/0658 73/37.9 |
| 2012/0064845 A1* | 3/2012 | Smith | H04M 1/05 455/90.2 |
| 2013/0035608 A1* | 2/2013 | Goldstein | A61B 5/121 600/559 |

\* cited by examiner

EARPIECE SYSTEM

CROSS-REFERENCE TO RELATED APPLICATIONS

This Non-Provisional Patent Application claims benefit of U.S. Provisional Application 61/154,502 filed Feb. 23, 2009, entitled "Earbud Adapter System", incorporated herein.

BACKGROUND

Portable music players and portable telephones are becoming increasingly common. Owners of these and similar devices often prefer to use them in conjunction with personal sound delivery devices. These devices are worn, for example, while driving (e.g. telephone headset), exercising, traveling, or studying or the like.

An earbud herein means a personal sound delivery device that fits substantially within the outer ear and which comprises an acoustic emitter. An earbud adapter herein means a physical adapter that first, physically and acoustically connects to an earbud and second; physically and acoustically connects to the user's ear. An earbud adapter does not include an acoustic emitter. An earpiece herein refers generically to an earbud and/or an earbud adapter.

Nearly all music players and portable phones have earpieces as a standard accessory, but these one-size-fits-all earpieces often do not stay in the user's ears or become uncomfortable over time.

Proper fitting earpieces can provide the benefit of ambient noise isolation or suppression similarly to how earplugs block sound. However, stock earpieces often do not fit well enough to accomplish this.

In an attempt to address the above described earpiece fit problems some companies offer kits of different size earbud adapters. The user selects, through a process of trial and error, the earbud adapter that fits his ear the best. While the probability of a better fit is thus increased, it is still inadequate because the variation in human ear anatomy is too great to be accommodated with a kit that is necessarily limited in its range of shapes and sizes. Furthermore, this approach requires the user to try on each earbud adapter and determine, sometimes over several hours use, if it provides the best fit. Finally, once the optimal earbud adapter is selected, the remaining ones are useless and this results in material waste.

Some companies provide a single flexible or compliant earbud adapter where the user is able to adjust its shape and size and/or the material is able to be compressed and then expand to conform to the inner surfaces of the user's ear anatomy. This flexibility or compliance partially addresses the above mentioned problems with kits, but the extent of the flexibility or compliance is necessarily limited to provide optimal results for a small range of anatomy centered on the average ear. When purchasing this product, the user will typically not know in advance whether his ears will fall within the range of the adapter's accommodation.

To solve the above mentioned problems other companies supply full custom earbuds or earbud adapters. They do this by first injecting a soft material into the user's ear to form a physical impression or mould. The mould supplies the ear shape information that is then used to manufacture the custom fitted earbud or earbud adapter. While this full custom approach solves many of the problems outlined above, it requires a significant amount of skilled labor which elevates the production cost. Production costs are further increased because the full custom approach necessarily precludes mass production. Additionally, the user must undergo the moulding process which can be uncomfortable, scary and time consuming. And finally, the user must wait several business days while the custom solution is built and shipped.

For these and other reasons, there is a need for the present invention.

SUMMARY

In accordance with disclosed embodiments, a system and method for providing earpieces includes an inventory of earpieces having a plurality of parameters and a device for making a non-contact ear measurement. An earpiece is selected from the inventory based on the non-contact measurement.

DETAILED DESCRIPTION

In the following Detailed Description, reference is made to the accompanying drawings, which form a part hereof, and in which is shown by way of illustrating specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

In general, disclosed embodiments employ ear measurement databases to optimize the parameters such as shapes and sizes of mass produced earbuds and earbud adapters. A simple-to-use, non-contact scanning apparatus measures the shape and size of a customer's ears and those measurements are used to determine which of the mass produced, prefabricated earbuds or earbud adapters are most suitable for that customer. In an additional aspect, newly available shape and size data acquired by the scanning apparatus are used to further optimize the ear shape and size databases.

Below, reference is made to Proximate and Remote physical inventories. Proximate Inventory is physical stock that is close enough to the point of sale that delivery of items from that stock to the purchaser can be accomplished without having to ship those items. Typically, Proximate Inventory will be held within the same retail store where the sale is made. However, it is envisioned that Proximate Inventory might be held at a single distribution point within an agglomeration of stores, such as a mall, so that delivery of physical product can be centralized even when several points of purchase are distributed within the mall. Remote Inventory is physical stock that is distant enough from the point of purchase that delivery of items to the purchaser must be accomplished by shipping.

Figure 1:
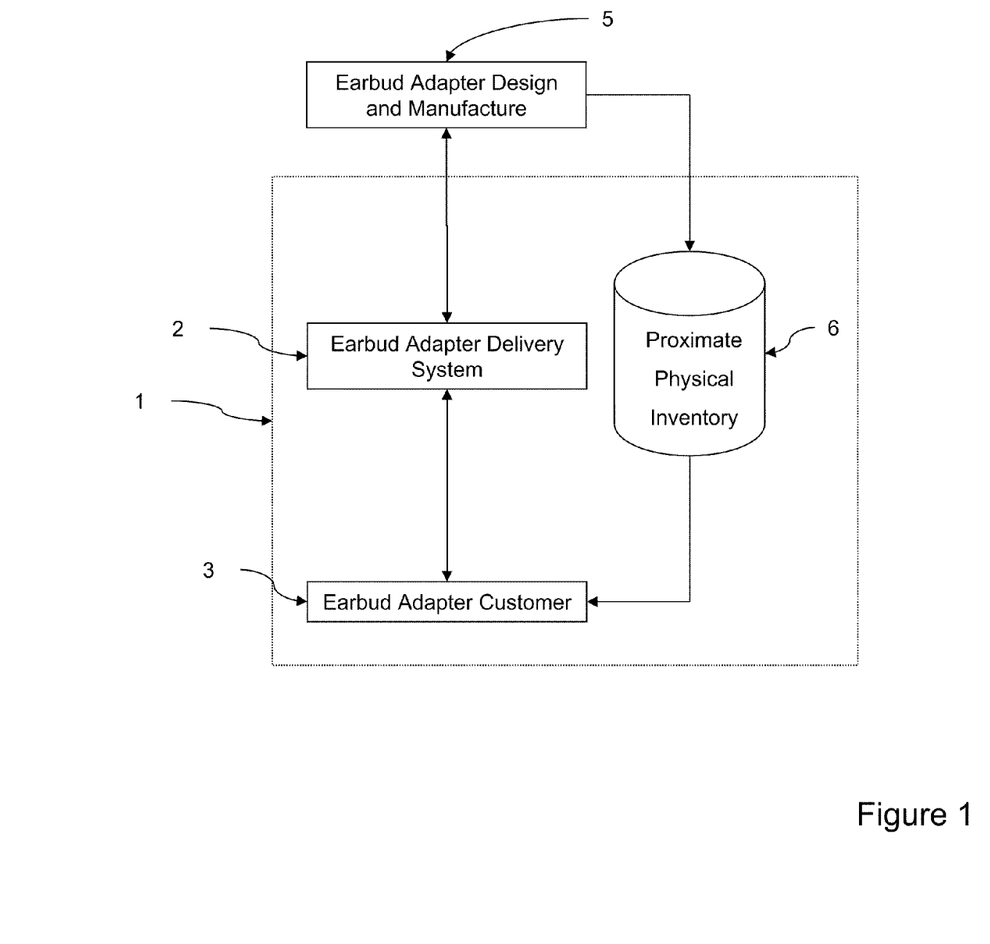
FIG. 1 shows how the system of this invention operates in a world context.

Referring to FIG. 1, an embodiment of an Earpiece Delivery System 2 scans or measures Earpiece Customer's 3 ears and selects and delivers earpieces to customer 3 from Proximate Physical Inventory 6 based on the ear measurement. In some embodiments, all of the systems enclosed in outline box 1 are co-resident at the point of customer contact, typically in a retail setting.

Figure 2:
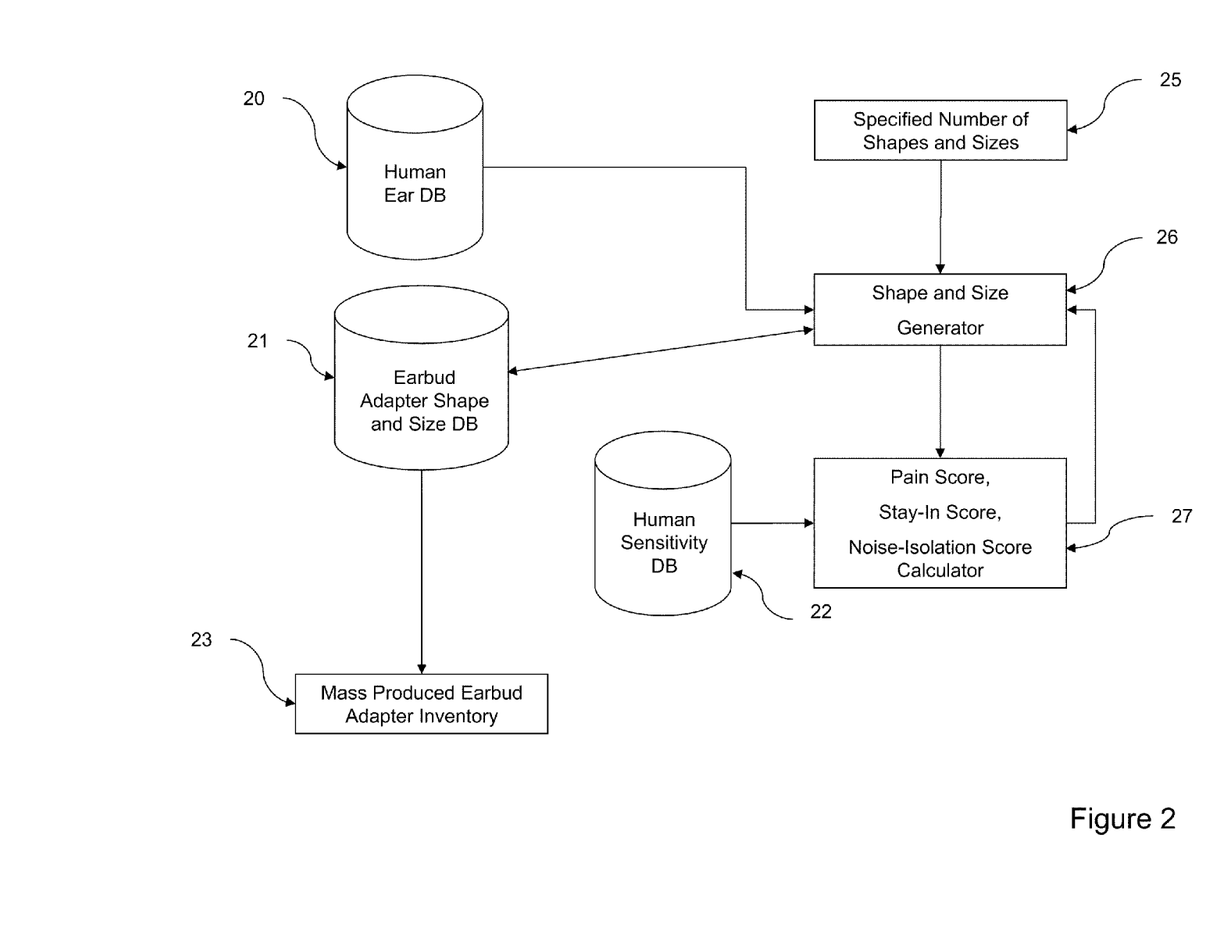
FIG. 2 illustrates how ear shape and size databases can be used to optimize the shapes and sizes of specified number of earpieces.

Referring to FIG. 2, Human Ear Database 20 includes measurements such as shape and size of relevant ear anatomy. These data can be purchased from research institutions or generated from scratch by scanning human ears with a suitable scanner, such as a three dimensional scanner. A Shape and Size Generator algorithm 26 accesses the shape and size data from the Human Ear Database 20 and, with limitations imposed by the Specified Number of Shapes and Sizes parameter 25, constructs the Earpiece Shape and Size Database 21. To do this, the Shape and Size Generator algorithm 26 utilizes, for example, the results of predictive Pain Score, Stay-In Score and Noise-Isolation Score Calculator 27. This Calculator predicts the discomfort (Pain), the likelihood that the Earpiece will stay in (Stay-In) and the Noise-Isolation capability of each Earpiece in the Earpiece Shape and Size Database 21 given information about subjective sensitivity provided by Human Sensitivity Database 22. There are numerous ways for the above described system to generate the optimal Earpiece Shape and Size Database 21. One way is to use Principle Component Analysis (PCA) to compute the principle components of the anatomical variation of the Human Ear Database 20. The lower order principle components are a characterization of the most substantial variation within that database 20 and will therefore help determine how the Earpiece shapes and sizes should vary. These results will be weighted by the Pain, Stay-In and Noise-Isolation predictive calculator 27, which adds human subjective response to the purely arithmetic calculations provided by the above outlined PCA approach. Those skilled in the art will recognize that the above outlined approach is only one example of how to optimize Earpiece Shape and Size Database 21 and that such optimization can be considered a multidimensional minimization problem, a problem space with many public domain solutions methodologies. Blocks 26 and 27 may iterate until the Pain Score is minimized and the Stay-In and Fit scores are maximized. The Earpiece Shape and Size Database 21 is thus optimized for the ear shapes in Human Ear Database 20 in light of the Human Sensitivity Database 22 given the Specified Number of Shapes and Sizes 25. The Earpiece Shape and Size Database 21 is then used to build Mass Produced Earpiece Inventory 23.

Various aspects of the disclosed system may be implemented by a computer system having an appropriately programmed processor, associated memory, etc. The systems are not limited to any particular hardware, firmware, or software configuration. In the disclosed embodiments, the modules may be implemented in any computing or data processing environment, including in digital electronic circuitry (for example, an application-specific integrated circuit, a digital signal processor (DSP), etc.) or in computer hardware, firmware, device driver, or software. In some embodiments, the functionalities of the modules are combined into a single data processing component. In some embodiments, the respective functionalities of each of one or more of the modules are performed by a respective set of multiple data processing components.

Figure 3:
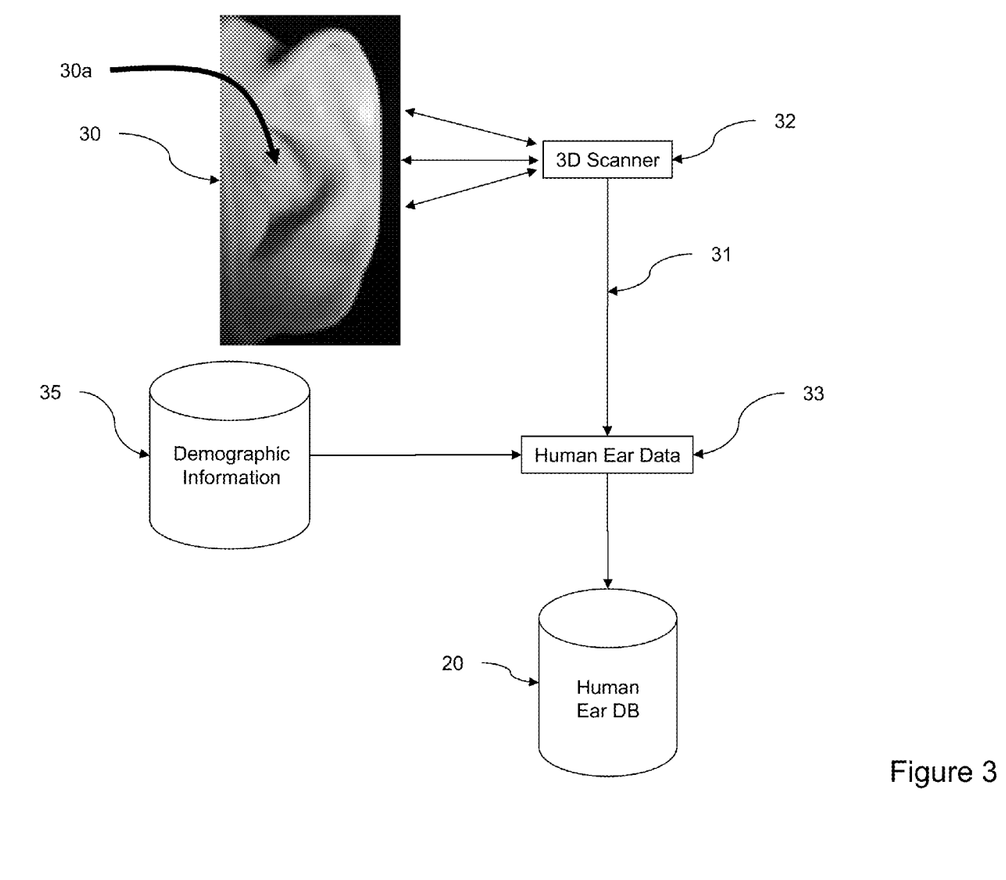
FIG. 3 illustrations how a non-contact scanner is used to scan a customer's ears.

Referring now to FIG. 3, 3D scanner 32 is used to generate three dimensional data 31 of a customer's ear 30. In the illustrated embodiment, non-contact 3D scanning is used because of the ear's sensitivity to pressure can result in physical pain, especially when said pressure is applied over time. Different anatomical points in the ear have differing sensitivity to pressure and one such area, the Cymba, is marked 30a.

A standard 2D image of the ear, acquired for example with an off-the-shelf digital camera, comprises brightness and/or color information of the ear in an array of pixels in a XY plane nominally coincident with the camera's focal plane. This 2D image does not comprise measurements along the physical axis, the Z axis, perpendicular to that focal plane. Although many algorithms attempt to infer Z axis physical measurements from standard 2D images, they are dependent upon many assumptions, are subject to many error sources and are therefore can be inaccurate and unreliable on the scales required to avoid pain causing pressures on regions of the ear like the Cymba 30a.

Numerous examples of 3D scanners 32 exist, but those which do not use Laser light are preferred for reasons of human safety. Scanners further able to characterize complex 3D topologies such as those present in the folds of the ear and in the outer portion of the ear canal are preferred. Additionally, scanners which are robust against misuse and can operate with no or little expertise are preferred. Three dimensional resolutions and accuracies on the order of 50 μm are preferred. Observation times short enough to make it unnecessary to fixture the human head are clearly preferred. Therefore, scanners using white light phase profilometry are preferred. An example of a 3D scanner that embodies all of these preferences has been disclosed in International Patent Application Publication No. WO2008/124397, which is incorporated by reference.

Figure 4:
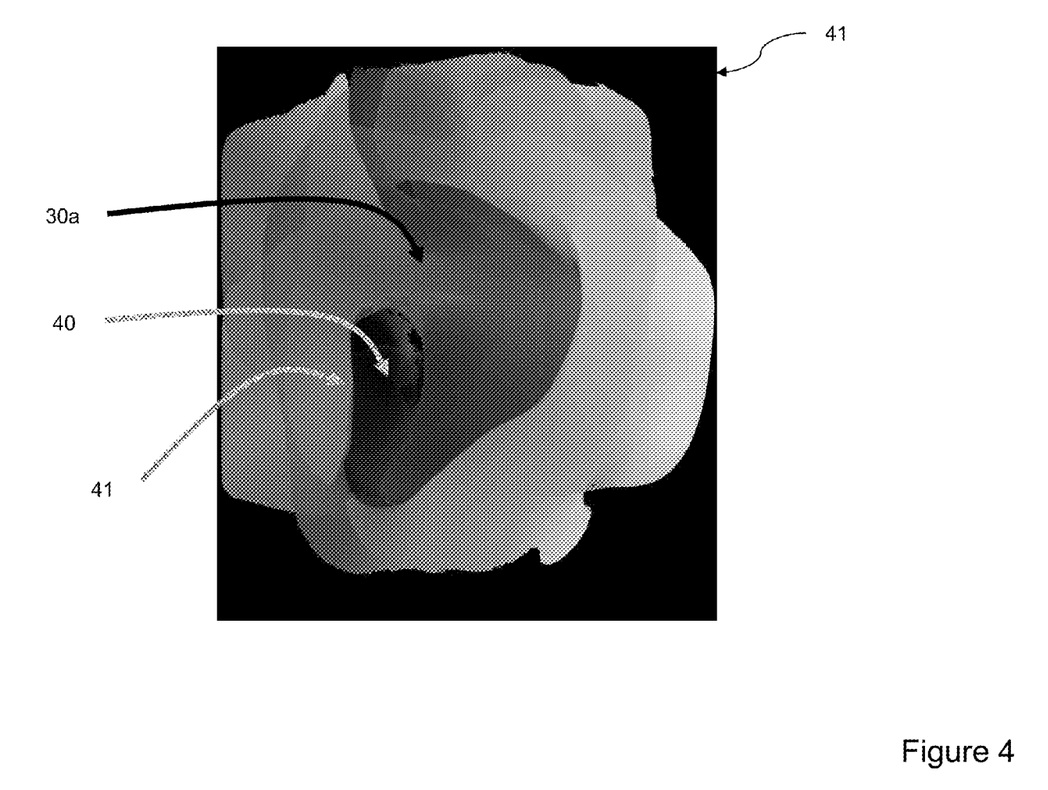
FIG. 4 is a 3D image of an ear, where the Z dimension is encoded as brightness.

FIG. 4 is a 3D image 41 of a human ear model acquired with a device in accordance with the above referenced and incorporated Patent Application where Z information is encoded as brightness. To elaborate, the brightness of each pixel is a direct measure of the distance from the focal plane of the point on the object imaged at that pixel; e.g. the brighter pixels correspond to surface features closer to the focal plane. The Cymba, at point 30a, has greater height (closer to the camera focal plane) than the bottom of the ear canal 40. The Tragus 41 has a greater height than the Cymba 30a. The height map 41 thus comprises a direct three dimensional characterization of the observed anatomy.

Referring again to FIG. 3, demographic information 35 is added to observed 3D ear data 31 to generate Human Ear Data 33 and thence Human Ear database 20. Clearly Human Ear database 20 will be enriched as more and more ears are scanned by the addition of new ear 3D topology data, but also by the inclusion of demographic information 35. Such demographic information includes the 3D system's locale (typically the retail store's address), the customer's approximate age, gender and ethnicity, the user's intended application, etc.

Figure 5:
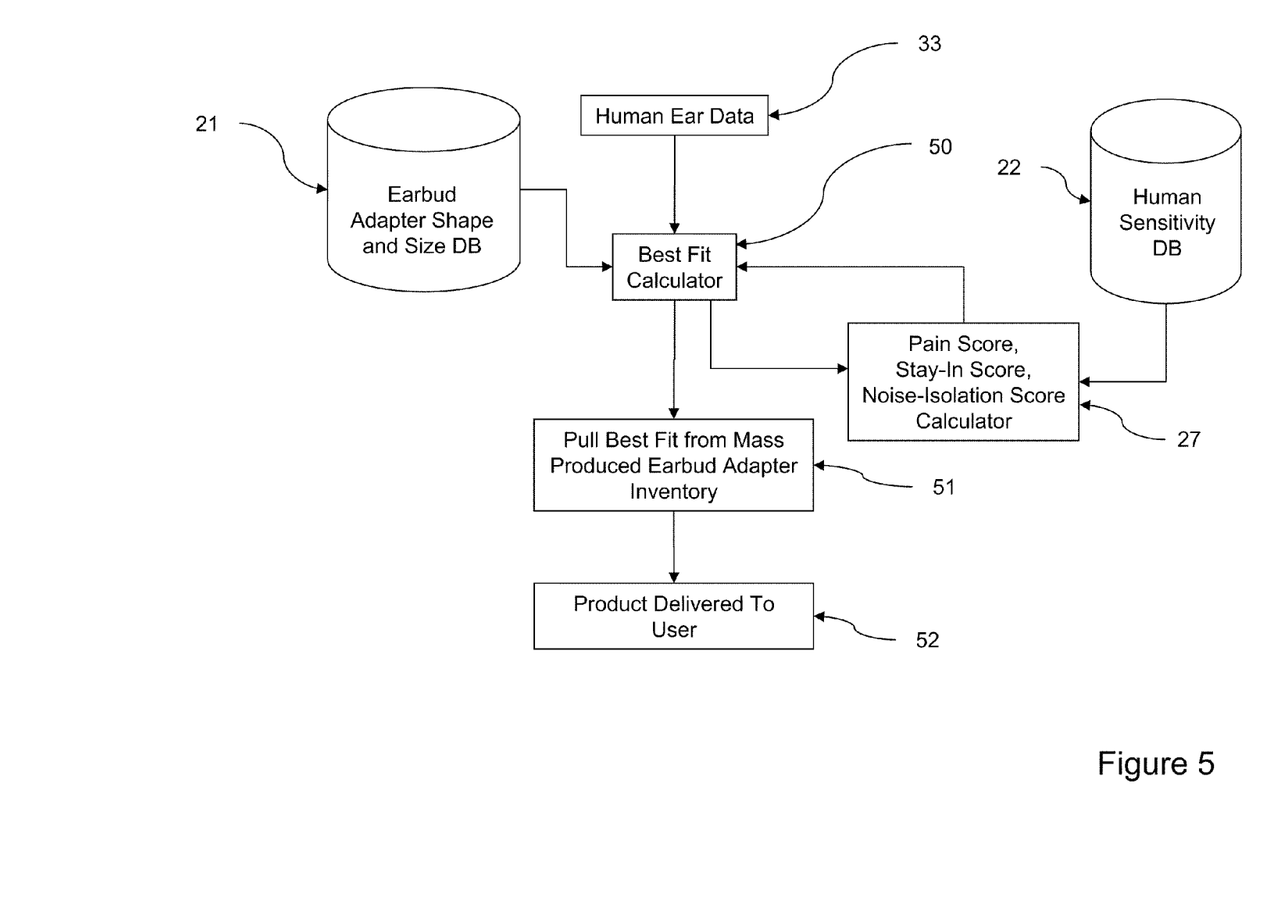
FIG. 5 illustrates how measurements from the non-contact scan are used to select which of the mass produced earpieces.

Referring now to FIGS. 3 and 5, a customer's ears 30 are scanned and Human Ear Data 33 are generated. Best Fit Calculator 50 determines the best fit by selecting the earpiece from Earpiece Shape and Size Database 21 that minimizes the Pain Score and maximizes the Stay-In and Noise-Isolation scores given the Human Ear Data 33 and the Human Sensitivity Database 22.

The selected best fit earpieces are then removed from physical inventory 51 and delivered to the user 52 either automatically or with human assistance.

It is possible that a limited range of physical inventory is available from stock held proximate the scanner 32 (Proximate Physical Inventory) and additional, more varied inventory is available from stock held at a centralized remote location (Remote Inventory, not illustrated). Thus, while FIGS. 3 and 5 describe an example of the process of selecting the best fit earpiece, it is possible that only a subset of the entire Earpiece Database 21 is available from Proximate Physical Inventory. If the best fit earpiece selected by Best Fit Calculator 50 is not held in Proximate Inventory, in some embodiments the processes illustrated in block 51 are performed at a centralized remote location (Remote Inventory) and block 52 is accomplished by shipping the earpiece to the user, where block 51 may involve the automatic transmission of ordering information to the centralized remote location.

Figure 6:
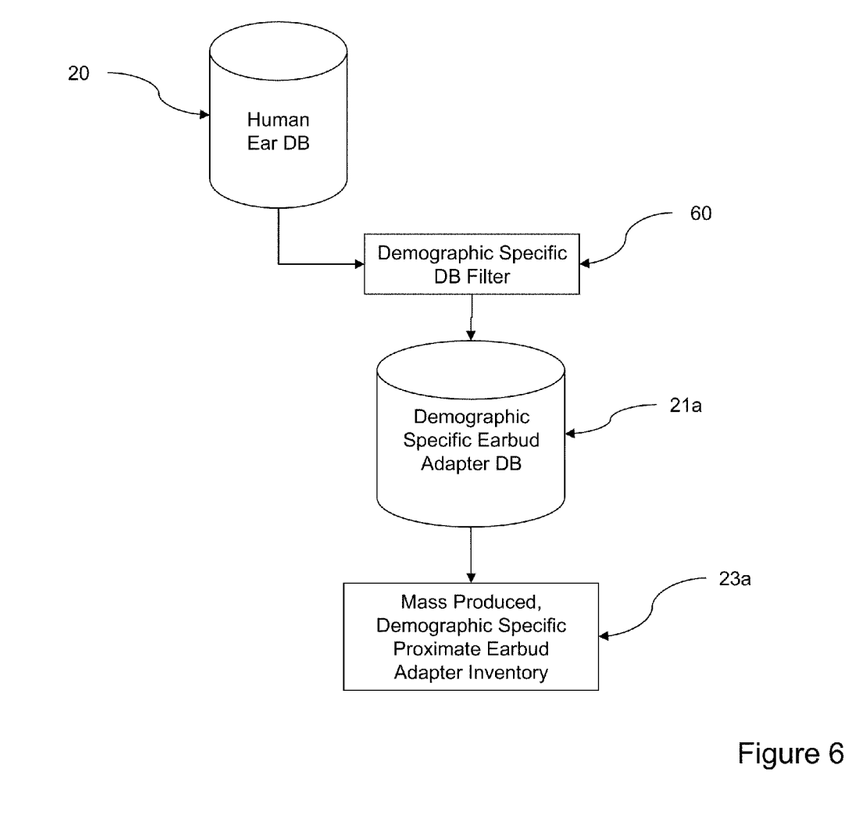
FIG. 6 illustrates how proximate physical inventory of earpieces can be optimized depending on demographics.

Refer now to FIG. 3 where data 31 from 3D scanner 32 and Demographic Information 35 are combined to form Human Ear Data 33 and then used to update the Human Ear Database 20. As mentioned, database 20 is enriched as more customers are scanned and there are several ways to use these enrichments. FIG. 6, for example, shows a filter used to optimize proximate physical inventory. Demographic Filter 60 operates so as to select a subset of ear shapes from Human Ear Database 20 to form a Demographic Specific Earbud Database 21a and a potentially unique Proximate Physical Inventory 23a. If, for example, a retail outlet implementing the system of this invention serves a predominantly younger population then, at least initially, Proximate Physical Inventory 23a could be optimized for sizes and shapes representative of that population. Thus, the probability that the best fit earpiece is in proximate inventory is increased.

As each site's sales volume accumulates its optimal proximate inventory will evolve accordingly; certain ear sizes and shapes will occur more frequently and other sizes and shapes will occur less frequently. It is anticipated that, over time, each site's actual sales history will come to dominate the optimization of proximate inventory and that demographic information such as age, while important initially, will become redundant.

Figure 7:
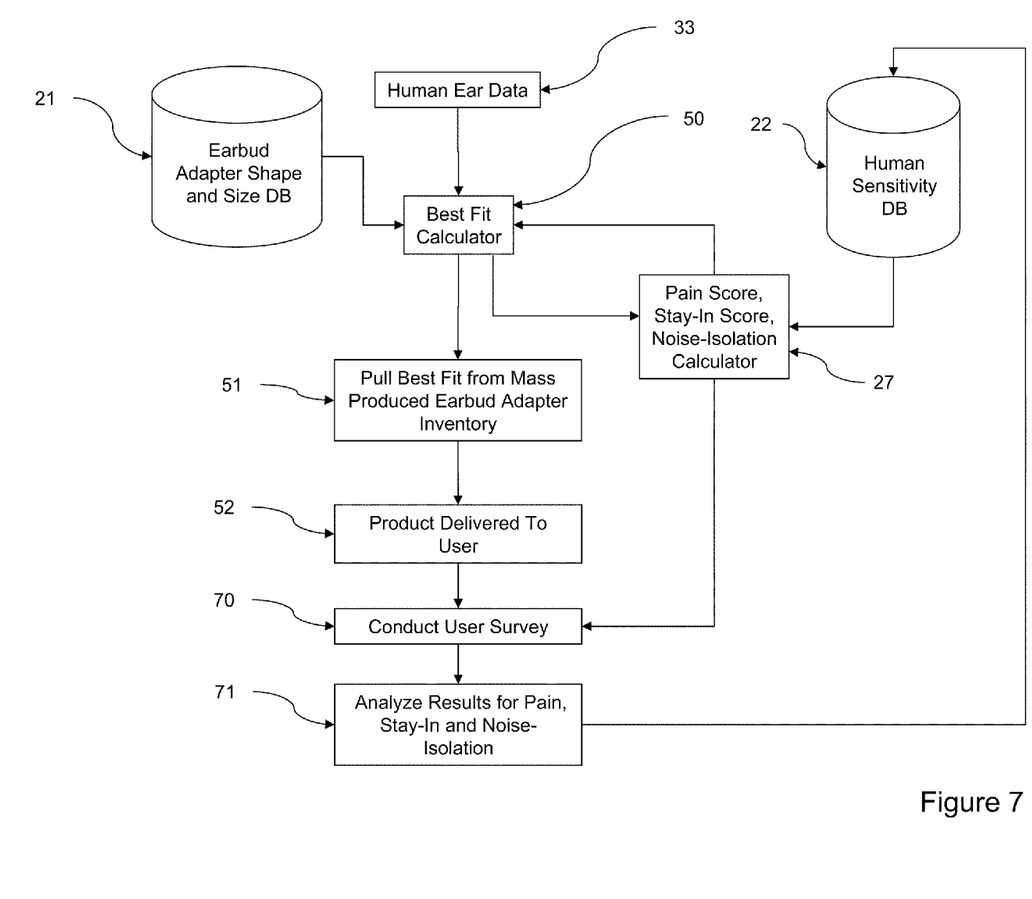
FIG. 7 illustrates a way to use feedback from users to optimize the Human Sensitivity database.

Referring now to FIG. 7, Human Sensitivity Database 22 is updated based upon User Survey 70 and Results Analysis 71. Thus the ability of Calculator 27 and Database 22 to predict Pain, Stay-In and Noise-Isolation scores can be improved with use. Said predicted scores must be accurate in order for the system of this invention to provide a high likelihood of a satisfactory customer experience.

It is envisioned that semi-custom earbuds, comprising acoustic emitters, can be delivered to users in ways similar to those described hereinabove.

In summary, the disclosed system and methods deliver semi-custom earbuds and/or earbud adapters to users based upon a measurement of the user's ears making it unnecessary to take a physical impression of the user's ears. The earpieces can be mass produced and therefore inexpensive when compared to full-custom solutions. Physical inventory is kept proximate each scanner and also at one or more locations remote from the scanner. Proximate Inventory is optimized for demographics and/or sales history and spans a wide range of ear anatomy so that the probability that a customer's optimal earpieces are in Proximate Inventory is high. When Proximate Inventory does contain the optimal earpieces, delivery to the customer is immediate. If the optimal semi-custom earpiece is not in Proximate Inventory, the Remote Inventory can be accessed to deliver the optimal earpieces to the user. The combined inventories of these semi-custom earpieces spans a wide enough range of anatomy with enough shape and size resolution so that discomfort and pain are minimized, the ear pieces will stay in the users' ears and ambient sound is well suppressed, all without requiring the user to try a number of ear pieces from a kit of limited selection.

What is claimed is:

1. An earbud delivery system comprising:
an earbud system including a three-dimensional scanner, a calculator and a processor, the three-dimensional scanner configured to generate a non-contact ear measurement for a user's ear, the non-contact ear measurement including a size measurement and a shape measurement for the user's ear; the calculator for calculating at least one factor for each earpiece within an inventory of earpieces based on the non-contact ear measurement from the three-dimensional scanner, the at least one factor is selected from the group consisting of: a pain score, a stay-in score and an ambient sound suppression score; and
the processor configured to select an earpiece from the inventory of earpieces based on the non-contact ear measurement from the three-dimensional scanner and the at least one calculated factor from the calculator.

2. The system of claim 1, wherein the three-dimensional scanner comprises a camera for generating the non-contact ear measurement.

3. The system of claim 1, wherein the non-contact ear measurement is generated based on a three-dimensional image of the user's ear is generated from the three-dimensional scanner.

4. The system of claim 1, further comprising a computer system including:
an earpiece parameter database for storing earpiece parameter data; and
wherein the processor is further configured to select the earpiece based on the earpiece parameter database and the non-contact ear measurement.

5. The system of claim 1, wherein the inventory of earpieces includes a first inventory situated proximate to the three-dimensional scanner to generate the non-contact ear measurement and a second inventory situated remote from the three-dimensional scanner to generate the non-contact ear measurement.

6. The system of claim 1, wherein the earpiece is an earbud or an earbud adapter.

7. A system comprising:
an earbud system including a three-dimensional scanner, a calculator and a processor, the three-dimensional scanner configured to generate a non-contact ear measurement for a user's ear, the non-contact ear measurement including a size measurement and a shape measurement for the user's ear;
the calculator configured to calculate at least one factor for each earpiece from a plurality of earpieces where each earpiece is associated with a plurality of parameters, the calculator calculating the at least one factor based on the non-contact ear measurement and the plurality of parameters for each respective earpiece and wherein the at least one factor is selected from the group consisting of: a pain score, a stay-in score and an ambient sound suppression score; and the processor configured to select an earpiece from the plurality of earpieces based on the non-contact ear measurement and the at least one calculated factor.

8. The system of claim 7, wherein the non-contact ear measurement is generated based on a 3D image of the user's ear obtained from the three-dimensional scanner.

* * * * *